United States Patent

Wallstén et al.

[11] Patent Number: 5,957,962
[45] Date of Patent: Sep. 28, 1999

[54] BALLOON CATHETER FOR HYPERTHERMIA TREATMENT

[75] Inventors: Hans I Wallstén, Denens; Jerome Duc, Corseaux, both of Switzerland

[73] Assignee: Wallsten Medical S.A., Denes, Switzerland

[21] Appl. No.: 08/836,750

[22] PCT Filed: Nov. 20, 1995

[86] PCT No.: PCT/SE95/01375

§ 371 Date: Jun. 13, 1997

§ 102(e) Date: Jun. 13, 1997

[87] PCT Pub. No.: WO96/15740

PCT Pub. Date: May 30, 1996

[30] Foreign Application Priority Data

Nov. 21, 1994 [CH] Switzerland .......................... 9404022

[51] Int. Cl.⁶ ...................................................... A61F 7/00
[52] U.S. Cl. ........................ 607/104; 607/105; 607/113; 606/27
[58] Field of Search .................... 606/27–31; 607/96, 607/101–2, 104–5, 113

[56] References Cited

U.S. PATENT DOCUMENTS

| | | | |
|---|---|---|---|
| 3,742,960 | 7/1973 | Dye et al. ............................... | 604/247 |
| 4,638,805 | 1/1987 | Powell ..................................... | 604/97 |
| 5,024,668 | 6/1991 | Peters et al. ............................ | 606/194 |
| 5,269,758 | 12/1993 | Taheri ..................................... | 606/27 |
| 5,449,343 | 9/1995 | Samsone et al. ........................ | 604/96 |
| 5,460,628 | 10/1995 | Neuwirth et al. ....................... | 606/27 |
| 5,683,410 | 11/1997 | Samson ................................... | 604/96 |

FOREIGN PATENT DOCUMENTS

WO 91/05528  5/1991  WIPO .
WO 93/05737  4/1993  WIPO .

*Primary Examiner*—Robert L. Nasser
*Attorney, Agent, or Firm*—Burns, Doane, Swecker & Mathis, L.L.P.

[57] ABSTRACT

Device for carrying out heat treatment so-called hyperthermia, in a body cavity or duct comprising a catheter having an elongate front part (3) intended for insertion into said cavity or duct provided with a central tube (9) and a flexible and/or elastic balloon (7) surrounding said central tube in a liquid-tight manner, further comprising an axially operating first inlet (11) at the proximal end of the central tube and at least one outlet from the central tube intended for the supply of said medium under pressure to the balloon for the expansion thereof. The device is characterized in that said central tube (9) at its distal end extends at least up to the forward inner wall of the balloon to which it is fixed, said device in connection with the distal end of the central tube (9) being provided with a valve (33; 33') enabling discharge of gas from the interior of the balloon (7) through at least one gas outlet arranged at said distal end.

21 Claims, 2 Drawing Sheets

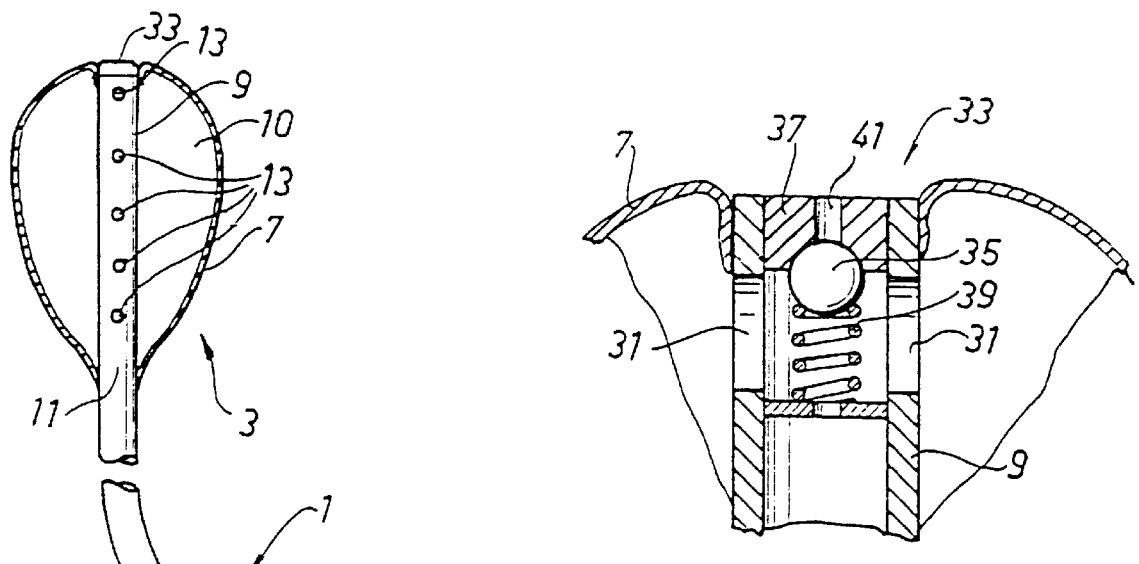
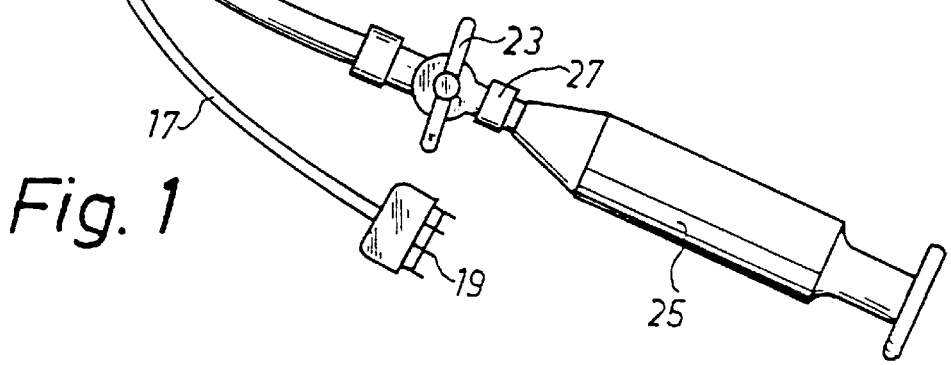
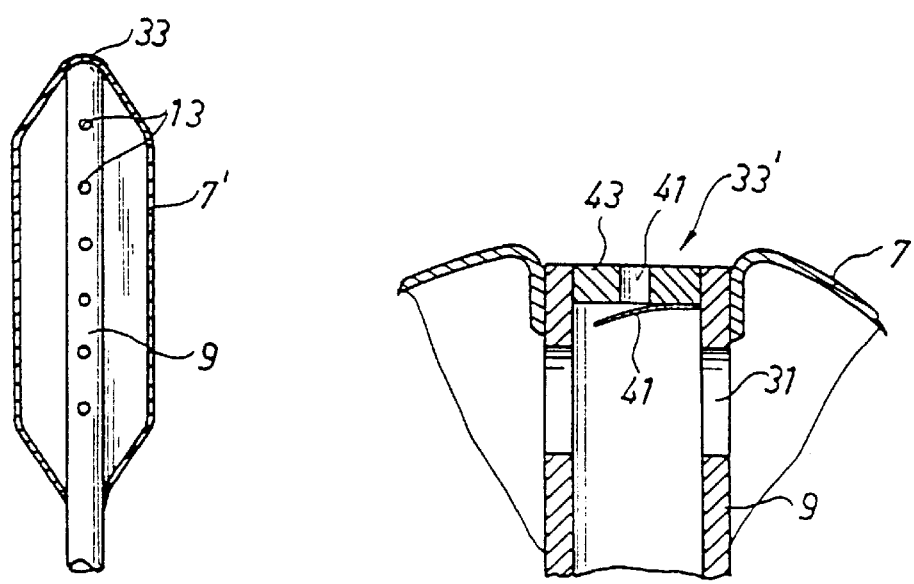

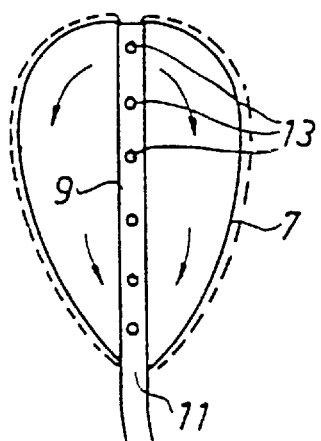
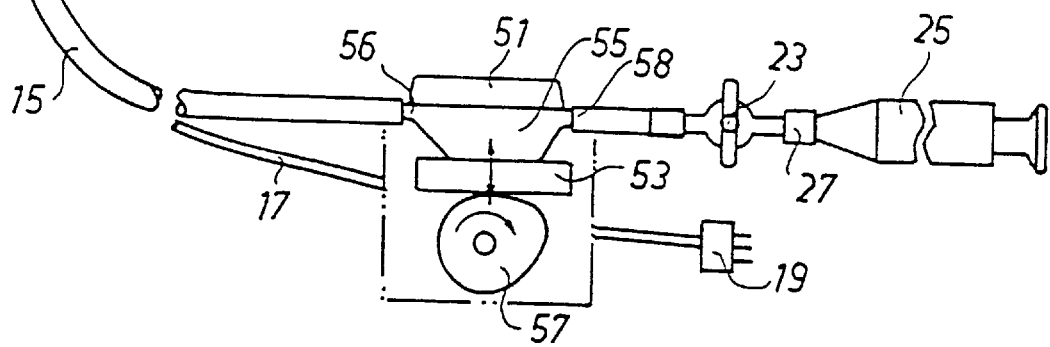
Fig. 5
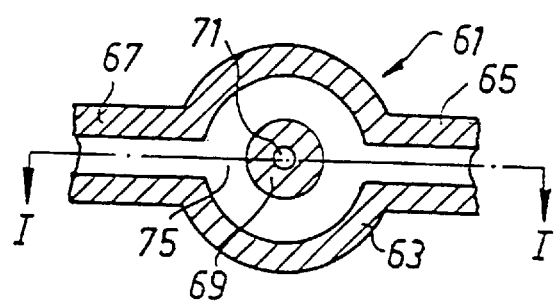
Fig. 6
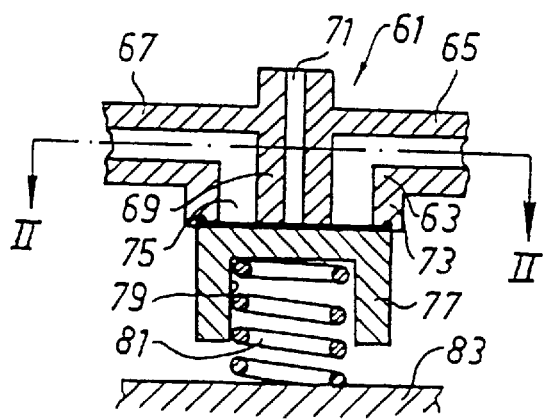
Fig. 7

BALLOON CATHETER FOR HYPERTHERMIA TREATMENT

The present invention relates to a device for carrying out heat treatment, so called hyperthermia, in a body cavity or duct. The device in question can be said to be a so called balion catheter for carrying out thermal treatment of areas in a body including man.

BACKGROUND OF THE INVENTION

In balloon catheters of this type heating of heat medium, frequently a liquid which after insertion of the catheter balloon into the organ to be treated, is used to expand the balloon. The heating can take place by an element positioned in the balloon for the transfer of heat to the liquid and further on to the inner calls of the cavity, and in certain designs the liquid is brought to circulate in the expanded balloon by means of some form of pumping system. Alternatively, the heating medium can be externally heated and then introduced into the balloon. A number of different types of balloon catheters for heat treatment of body cavities are known, and in certain cases it has been suggested that the heated liquid is circulated within the balloon for reaching an even heat distribution in the expanded balloon and efficient heat transfer to surrounding tissues.

In U.S. Pat. No. 4,949,718 there is described a balloon catheter for the destruction of uterus mucosae by means of heating, the heating taking place through a liquid which is heated by means of an electric heating element comprising a spiral surrounded by a screen provided with holes to a temperature near or at the boiling point of the liquid. In this system a certain self-circulation will be obtained in view of the fact that the liquid is heated to a temperature near its boiling point. The disadvantage of this device is, however, that sudden formation of steam can increase the pressure in the cavity in an uncontrolled manner resulting in risk for rupture in the uterus muscle. Furthermore, no efficient heat transfer to the surrounding tissues will be obtained in view of lack of a forced circulation of the liquid.

In U.S. Pat. No. 4,160,455 there is described a device for the heat treatment of a body cavity where a heating medium in the form of a liquid is heated by electric resistance elements and is circulated within an enclosure for the distribution of heat and improvement of the heat transfer to the surrounding. The circulation is provided by means of a bellows system providing an oscillating movement, and by a system of back valves in a housing surrounding the heating element the oscillating movement of liquid is transferred to a circulating movement.

In PCT-application SE94/00208 there is described a balloon catheter for hyperthermal treatment of body cavities, for example uterus, where a balloon, after insertion into the cavity, is expanded by means of a liquid heating medium injected into the rear or proximal end of the catheter by means of for example a syringe. The heating device consists of an auto-regulating material having a so called Curie point and the energy supply is carried out in an electric way. This auto-controlling material may either be constituted by a ferromagnetic metal alloy which is wirelessly heated to the Curie point by a magnetic field affecting the material. The Curie point has been selected for providing the desired therapeutic effect. An alternative heating element according to this prior art is one wherein the auto-controlling material consists of a number of thin lamellae of so called PTC elements having a selected Curie point placed in the cylindric housing, heating taking place by means of an electric current under low voltage.

In the device according to said PCT-application the liquid heat medium is circulated in the balloon so that efficient heat transfer to surrounding tissue is provided, since otherwise the auto-controlling character of the material would result in shut down of the elements and thereby lack of release of sufficient power. Also in this case the circulation of the heat medium takes place by imparting to same a reciprocating movement which is then converted to circulation in the expanded balloon by the use of a system of counter-positioned back valves. Also in this case the circulation contributes to a more even heat transfer to the surrounding tissues, which is essential for providing the desired impact.

However, it has been found that the known devices are associated with serious disadvantages. Generally, these consist in the formation of air pockets at certain positions in the system when the device is filled with the liquid by which heating shall take place, and such air pockets when assembled in the balloon result in impaired heat transfer so that the desired effect will not be obtained. In such systems based on forced circulation, for example according to U.S. Pat. No. 4,160,455, air pockets result in substantially reduced pumping capacity in view of the compressibility of the air.

SUMMARY OF THE INVENTION

The present invention has for its object to provide a new device for carrying out heat treatment, so called hyperthermia, while maintaining an efficient heat transfer from the heating medium.

Another object of the invention is to provide a device for carrying out hyperthermia, where the arisal of air pockets in connection with the filling of the device with a liquid heating medium is essentially prevented.

Yet another object of the invention is to provide a device for carrying out hyperthermia in which the filling of liquid heat transferring medium takes place in one single operation in a simple manner.

A further object of the invention is to provide a device where the part which is contaminated in connection with the use thereof is suited for mass fabrication at a reasonable cost and can thus be disposed of after use.

A further object of the invention is to provide a device where there is arranged at the distal end of the catheter a central rigid part centered within the balloon so that contact between the outer walls thereof and the inner walls of the balloon is avoided.

Yet an object of the invention is to provide a pulsating pressure in the heat transferring medium so that uniform treatment and improved heat transfer will be obtained.

For these and other objects which will be clear from the following disclosure the invention provides for a device for carrying out heat treatment, so called hyperthermia, in a body cavity or duct, comprising a catheter with an elongate front part intended for insertion into said cavity or duct and provided with a central tube and a flexible and/or elastic balloon surrounding said central tube in a liquid-tight manner, further comprising an axially operating first inlet at the proximal end of the central tube for the supply of a heat transferring medium to the central tube, and at least one outlet from the central tube intended for supply of said medium under pressure to the balloon for the expansion thereof.

The device according to the invention is characterized in that said central tube at its distal end extends at least up to the forward inner wall of the balloon to which it is fixed, said device in connection to the distal end of the central tube being provided with a valve enabling release of gas from the interior of the balloon through at least one gas outlet arranged at said distal end.

This valve through which remaining gas in the system can be discharged or evacuated is suitably some type of back valve, for example a so called fizz valve which can be exteriorly actuated, but may alternatively be constituted by a valve with narrow ducts or capillaries allowing the passage of gas but preventing the passage of liquid.

Conceivable fizz valves are valves in the form of a ball valve with a spring-actuated ball and a seat cooperating therewith, but may also be constituted by a fizz valve with a so called flap and an associated seat, said flap being exteriorly releasable from the seat for discharge of gas from the interior of the balloon, and which in an unloaded condition reverts to sealing position, for example by inherent springing.

In a preferred embodiment of the device according to the invention said outlet can simultaneously suitably constitute a gas outlet.

A particular embodiment of the device according to the present invention is characterized by means for providing a pulsating pressure of the heat transferring medium, whereby a more uniform heat treatment and improved heat transfer can be obtained.

Said means suitably comprises a chamber of variable volume which via an outlet is connected to said first inlet and which is arranged to periodically be imparted a reduced and an enlarged volume, respectively, said chamber and any other chambers with inlet and outlet in the catheter being designed in such a way that the highest point of each chamber is positioned at the same level or lower than the highest point of the transition of the chamber to the outlet, whereby the leaving behind of air or other gas when the heat transferring medium is supplied will be avoided.

It is preferred that said chamber is defined by a compressible and elasticly reverting container which can be brought to periodic compression from the outside. Said means may further comprise a reciprocating element providing periodic compression.

For safety reasons the device is further suitably provided with a safety valve arranged in the catheter which has for its function to eliminate the risk for too high overpressures in the system.

In embodiments with heating by means of a heating element positioned inside the balloon said heating element may be of any type, particularly based on heating by the supply of electric power, but it is particularly preferred to use heat releasing elements of the auto-controlling type, for example a so called PTC-type. With regard to details concerning the type of element, the arrangement for providing circulation of the heat transferring medium and possibly other details reference is made to the above-mentioned PCT-application SE94/00208, the whole disclosure of which is incorporated herein by reference.

In the present disclosure the expression "distal" and "proximal" are used in the meaning "forward" and "rear", respectively, i.e. related to the operator of the instrument or device.

DETAILED DESCRIPTION OF THE INVENTION

The present invention will now be further described by exemplifying, non-limiting embodiments in conjunction with the appended drawings, wherein:

FIG. 1 shows diagramatically an embodiment of the device according to the invention illustrating the principle design of the device;

FIG. 2 shows in a section a detail of a valve for the evacuation of gas from the system;

FIG. 3 shows an alternative valve design; and

FIG. 4 shows an alternative embodiment of the expandable balloon;

FIG. 5 shows an alternative embodiment of the device according to the invention; and FIGS. 6 and 7 show in sections a plan view and a side view, respectively, of a safety valve intended to be placed in the balloon catheter according to the invention.

FIG. 1 shows diagramatically an embodiment of a balloon catheter according to the invention, said embodiment being shown in a very simplified form. The balloon catheter generally designated 1 comprises a distal part 3 provided with an expandable balloon 7 of for example highly elastic silicon, a central tube 9 having an axially proximal inlet 11, outlet openings 13, the two latter openings enabling introduction of a heat transferring medium to the balloon. The distal part 3 further comprises suitable heating means, such as heat-releasing element not shown.

The catheter tube 15 comprises inter alia ducts for the supply of liquid medium to the balloon 7 and conduits for the supply of electric power to the element 10 and for the transmission of signals from any sensors for pressure and temperature which can be placed in association with the balloon. In the rear part of the catheter said electric conduits are separated in the form of a special cable 17 which, via a coupling box 19, can be connected to some type of control unit. A closure valve 23 connected to the proximal end of the tube, said valve simultaneously constituting the proximal end of the catheter. In FIG. 1 there is also shown a filling device 25 for the introduction of liquid medium in the form of a conventional syringe with piston, which is connected to the valve 23, for example via a so called luer coupling 27.

The procedure for introducing heat transferring liquid medium into the device shown in FIG. 1 is the following. The catheter with the balloon 7 in an unexpanded state in a sterile package is removed from the package, the syringe 25 is completely filled with the liquid to be used as a heat transferring pressure medium and is then connected to valve 23 via coupling 27. The catheter filled with air is suitably held in a vertical position with the distal part pointing upward, as shown in FIG. 1. When the piston of syringe 25 is moved forward the liquid will progressively move forward and upward at the same time as the air enclosed in the catheter starts to fill the balloon without air remaining in the system. The filling is concluded when the liquid level has reached a certain position 10 in the balloon 7, as shown in FIG. 1. Above this level the air previously found in the catheter will be collected under a certain pressure around central tube 9.

The air enclosed in the balloon 9 can now be removed through a valve arranged in the distal end of balloon 7. Such device is illustrated in FIG. 2, where the distal part 45 of the central tube 9 is provided with outlet openings 31 corresponding to the opening 13 as shown in FIG. 1. In the distal end of central tube 9 a second valve 33 is arranged which has the form of a ball 35 which engages an associated seat 37 by a spring 39. In the seat 37 of valve 33 an outlet opening 41 is arranged.

When all air has been collected under pressure at the distal part of the balloon in the manner described above valve 33 is opened by inserting a fine needle through opening 41 so that complete deairiation of balloon 7 can take place.

An alternative valve device allowing deairiation of balloon 7 can be constituted by a fibre plug provided with fine ducts or capillaries which has the ability of letting through only gas but not allowing passage of liquid. An example of a suitable material for such fibre plug is HDPE from POREX Technologies, Georgia, USA, having an average pore size of 60 µm, pore volume range 45–55%. In order to prevent possible reentrance of air in the evacuation of the balloon a back valve, for example a flap, can be arranged which allows flow out from the balloon but not in the opposite direction.

After the catheter has been filled with liquid medium in the manner described above it can be connected to a control unit which can include inter alia means for control and steering of the treatment procedure with regard to temperature, pressure and time, and a power source in the form of for example a low voltage DC battery.

In FIG. 3 there is shown an alternative embodiment of valve 33', which is provided with a so called flap 41 cooperating with a valve seat 43 containing a central opening 41. In the same way as in the embodiment according to FIG. 2 this valve 33' can be opened from the outside to the position of flap 41 shown in FIG. 3 with a pointed object, which enables air found in the upper end of balloon 7 to be evacuated. The flap 41 is suitably made of a spring material so that it returns to closed position by the inherent elasticity of the material. However, also here the closing position can be ensured by means of any sort of spring member, such as shown in FIG. 2.

The hyperthermia treatment is started by introducing the unexpanded but liquid-filled balloon into the cavity, for example uterus, whereafter the balloon is expanded to a suitable pressure by actuation of syringe 25 after opening of valve 23. After the reclosure of valve 23 the course of treatment is started by actuation from the control unit in that heating is started by supply of electric current via cable 17 to the heating element in the central tube 9 until the correct temperature has been reached. Control of temperature and control of pressure can take place in a manner known per se by cooperation between sensors in the distal part of the catheter and the control unit via cable 17.

FIG. 4 shows an alternative embodiment of the balloon 7'. In this embodiment the balloon is preshaped for adaptation to the intended use, for example for the treatment of urethra such as in connection with prostate problems. The balloon 7' is as before made of a flexible thin material, for example PET, but in this case with a restricted stretchability since the adaptation to the surrounding walls primarily takes place by the fact that the balloon has been given the desired shape in advance.

FIG. 5 shows a device corresponding to that described above in connection with FIG. 1 but which in the embodiment in FIG. 5 contains an arrangement for providing a pulsating pressure of the heat transferring medium. This arrangement includes a container 55 placed in line with the catheter somewhere between valve 23 and inlet 11. The container 55 is provided with an inlet 58 and an outlet 56 and is held between a fixed jaw 51 and a movable jaw 53. The movable jaw is imparted a reciprocating movement by means of an excenter 57 as shown with arrows in the figure.

Accordingly, the balloon catheter according to FIG. 5 when used can be operated with a pulsating pressure of the heat transferring medium, which provides a certain periodically varying volume of balloon 7 (indicated with a dashed line in FIG. 5), and in view of this pulsation of the heat transferring medium a more efficient heat transfer to the surrounding of the balloon will be obtained on the one hand and also a more uniform treatment result on the other hand. For example, at a puls frequency of 10 pulses per second a volume change of about 2 mL per puls will be provided in the system.

FIGS. 6 and 7 show in two sections diagramatically a safety valve intended to be positioned in the catheter in connection with the system containing heat transferring medium. The safety valve generally designated 61 may thus be positioned somewhere in the catheter circuit between the valve 23 and the inlet 58 of container 55, but this position is not of a critical importance.

With regard to FIGS. 6 and 7 there is shown in FIG. 6 a section taken along line II—II in FIG. 7, whereas FIG. 7 shows a section taken along line I—I taken in FIG. 6. The safety valve 61 shown comprises a valve housing 63 provided with an inlet 65 and an outlet 67. In the central part of valve housing 63 a vertical hub 69 is placed forming an annular zone for flow through valve housing 63. Hub 69 contains a central vertical passage 71 which is open at the upper end for discharge of medium and which at the lower end normally is sealed by means of a membrane 75 closing a part 73 of valve housing 63 protruding downwardly. On the lower side of the membrane there is found a backing in the form of an annular element 77 having a central recess 79 accomodating a spring 81 engaging against a support 83 shown diagramatically. By this spring 81 element 77 is pressed against membrane 75 by a certain predetermined pressure whereby the lower opening of passage 71 is held closed.

In the use of the balloon catheter the safety valve functions briefly as follows.

At normal working pressure of the heat transferring medium passage 71 is closed by the engagement of membrane 75 against the lower end of hub 69. If the pressure exceeds the normal working pressure so as to cause a safety risk the resistance of spring 81 will be overcome whereby the membrane 75 will be pressed downwardly under release of the lower opening of passage 71. This means that the pressure of the medium can be released in that heat transferring medium can flow out through passage 71. When the pressure returns to normal sealing against the passage 71 will again be obtained so that further quantity of heat transferring medium cannot be discharged from the system.

By the design of the safety valve 61 no problems with remaining air pockets will be encountered when filling the system with heat transferring medium since in the filling operation the annular space inside valve housing 63 is first filled with liquid, the air present in the system then leaving through outlets 67.

In connection to the embodiment shown in FIG. 5 with pulsating pressure of the heat transferring medium the central tube 9 with the outlets 13 may be supplemented in the following manner.

If in connection to openings 13 back valves are arranged which allow flow in only one direction and if said valves are placed counter to each other in openings 13 according to a certain system the pulsation obtained by the periodic change of volume of container 55 can provide circulation inside the central tube 9 and the balloon. Accordingly, if the three uppermost openings 13 in FIG. 5 are alloted back valves allowing flow only out from the central tube 9, and the three lowermost openings 13 are alloted back valves positioned in the opposite way there will be obtained in the pulsation of the medium a certain circulation inside the balloon in a manner indicated by the arrows in FIG. 5. It is also conceivable to arrange the back valves in connection with openings 13 so that they are pair-wise counteracting, whereby certain circulation in connection with adjacent pairs of openings 13 will be obtained.

Such back valves can be of a very simple kind, for example simple ball valves or valves with so called flaps which can provide sealing by inherent elasticity.

It should be observed that the invention is not restricted to the embodiments described above which can be modified in many ways within the scope of the appended claims. Such changes and modifications which are obvious to the skilled artisan can be made within the framework of the inventive idea which is reflected in the wording of the appended patent claims.

We claim:

1. Device for carrying out heat treatment in a body cavity or duct comprising:
   a catheter having an elongate front part intended for insertion into said cavity or duct provided with a central tube,
   a flexible and/or elastic balloon surrounding said central tube in a liquid tight manner
   an axially operating first inlet at the proximal end of the central tube,
   wherein at least one outlet from the central tube intended for the supply of a heat-transferring liquid medium under pressure to the balloon for the expansion thereof,
   wherein said central tube at its distal end extends at least up to the forward inner wall of the balloon to which it is fixed,
   said device in connection with the distal end of the central tube being provided with a manually actuable valve for selectively enabling displacement of gas from the interior of the balloon by said liquid medium through at least one gas outlet arranged at said distal end.

2. Device according to claim 1, wherein said valve is a valve which can be actuated from the outside.

3. Device according to claim 2, wherein said valve is a ball valve with a spring-actuated ball and a seat cooperating therewith.

4. Device according to claim 3, wherein said outlet also constitutes a gas outlet.

5. Device according to claim 3, further comprising means to provide a pulsating pressure of the heat-transferring medium, whereby a more uniform heat treatment and improved heat transfer can be obtained.

6. Device according to claim 3, further comprising a safety valve arranged in the catheter.

7. Device according to claim 2, wherein said valve comprises a flap with an associated seat, said flap being liftable from the seat for the release of gas from the interior of the balloon.

8. Device according to claim 2, wherein said outlet also constitutes a gas outlet.

9. Device according to claim 2, further comprising means to provide a pulsating pressure of the heat-transferring medium, whereby a more uniform heat treatment and improved heat transfer can be obtained.

10. Device according to claim 2, further comprising a safety valve arranged in the catheter.

11. Device according to claim 1, wherein said outlet also constitutes a gas outlet.

12. Device according to claim 1, further comprising: means to provide a pulsating pressure of the heat-transferring medium, whereby a more uniform heat treatment and improved heat transfer can be obtained.

13. Device according to claim 12, wherein said means comprises a chamber of variable volume which, via an outlet, is in connection with said first inlet, and which is arranged to periodically be imparted a reduced and an enlarged volume, respectively, said chamber and any other chambers with inlet and outlet in the catheter being designed in such a way that the highest point of each chamber is positioned at the same level or lower than the highest point of the transition of the chamber to the outlet, whereby the leaving behind of air or other gas when the heat-transferring medium is supplied will be avoided.

14. Device according to claim 13, wherein said chamber is defined by a compressible and elastically reverting container which from the outside can be brought to periodic compression.

15. Device according to claim 14, wherein said means comprises a reciprocating element providing periodical compression.

16. Device according claim 1, further comprising a safety valve arranged in the catheter.

17. A device for performing a heat treatment comprising:
   a central tube;
   an expandable balloon connected to, and surrounding at least in part, said central tube;
   an inlet to said central tube for providing a liquid medium thereto;
   an outlet from said central tube for conveying said liquid medium into said expandable balloon; and
   a manually actuable valve disposed within said central tube which is selectively openable and closeable to permit gas to be released from said expandable balloon.

18. The device of claim 17, wherein said manually actuable valve comprises a spring-actuated ball and a seat cooperating therewith.

19. The device of claim 17, wherein said manually actuable valve comprises a flap and an associated seat.

20. The device of claim 17, further comprising:
   means for providing pulsating pressure of said liquid medium.

21. The device of claim 20, wherein said means for providing pulsating pressure further comprises:
   a variable volume chamber which is connected to said inlet to adjust a pressure associated with said liquid medium.

* * * * *